United States Patent [19]

Higaki

[11] Patent Number: Plant 7,367

[45] Date of Patent: Oct. 23, 1990

[54] CACTACEAE PLANT NAMED DASHER

[75] Inventor: Harry Higaki, Hillsborough, Calif.

[73] Assignee: Bay City Flower Co., Half Moon Bay, Calif.

[21] Appl. No.: 340,562

[22] Filed: Apr. 19, 1989

[51] Int. Cl.[5] ..... A01H 5/00

[52] U.S. Cl. ..... Plt./88

[58] Field of Search ..... Plt./88.5, 88

*Primary Examiner*—Howard J. Locker

*Attorney, Agent, or Firm*—James R. Cypher

[57] ABSTRACT

The present invention relates to a new and distinct cultivar of Cactaceae Plant named "Dasher", obtained through cross-pollination of *Schlumbergera truncata* "Maria" and *Schlumbergera truncata* "Lavender Doll", distinguished from its closest commercial variety, known to me "Rudolph", and its parents by its more intense red flower color, a faster growth rate, larger flowers and phylloclades, better breaking propensity, more vigorous budding and flowering habit, upright and dense appearance and considerable resistance to nutrient deficiencies and fungus type diseases.

1 Drawing Sheet

BACKGROUND OF THE INVENTION

The invention relates to a new and distinct plant variety of the Cactaceae family which has been named *Schlumbergera truncata* "Dasher" by the inventor.

Certain plant varieties of the Cactaceae family, which are among those of the *truncata* species of the Schlumbergera genus, tend to bloom in the months of November and December in the Northern Hemisphere. Because of their blooming time they appear in the market primarily during the Thanksgiving and Christmas seasons, and hence the common name Christmas Cactus. During the Christmas season, a "reddish" colored bloom is often very desirable. There are many "reddish" colored varieties available on the market, but none of the varieties combine the characteristics of having an accelerated growth rate of two to three weeks earlier when in four inch size pots and four to five weeks earlier when in six inch size pots, good breaking, a compact growth habit and free budding and flowering characteristics. The "reddish" varieties that were available in the past are either slow growing with good breaking, and free budding and flowering characteristics, or fast growing with poor breaking, and low budding and flowering characteristics.

The main objective of the invention has been to develop a variety of the Cactaceae family with a "reddish" colored bloom that has a fast growth rate, a vigorous breaking propensity and is free budding and free flowering. Another objective has been to develop a variety that also has an upright and dense appearance, and has suitable resistance to nutrient deficiencies and fungus type diseases.

The present invention is the second new variety developed by me with the above objectives in mind, and the closest commercial cultivar in color and characteristics to the new variety, of which I am aware, is the first new Cactaceae plant developed by me, named Rudolph, U.S. Pat. No. P.P. 6,234. The "Rudolph" variety has a "reddish" colored bloom, good breaking, a compact growth habit and free budding and flowering characteristics. However, the growth of Rudolph is two to five weeks slower than "Dasher", in a 4" pot, and the flower and phylloclades size of "Dasher" is larger then Ruldolph's flowers and phylloclades.

The objectives of the invention have been obtained by the development of the new variety. The new variety was developed in a nursery located in Half Moon Bay, Calif., as a hybrid obtained through the cross-pollination of *Schlumbergera truncata* "Maria" and *Schlumbergera truncata* "Lavender Doll". "Maria" being the paternal parent and "Lavender Doll" the maternal parent. The seeds taken from the fertilized seed pod were cultivated at the Half Moon Bay nursery and, after observation of the seedlings, the hybridized plant of the new variety was selected and asexually reproduced by the inventor at the nursery by the propagation of stem cuttings taken from the original hybrid plant.

Through successive propagations, it has been recognized that specimens of the new variety resemble the parent varieties, but are distinguishable from the parents and other related varieties known to me, by a growth habit which is clearly visible in the specimens propagated and grown under nursery conditions at the Half Moon Bay location, as combining the following characteristics:

1. A more intense "reddish" colored bloom then "Rudolph".
2. A faster growth rate than both parents and "Rudolph".
3. Breaking propensity comparable to the maternal parent and better than the paternal parent.
4. A vigorous free budding and flowering habit comparable to the paternal parent and better than the maternal parent.
5. An upright and dense appearance.
6. Considerable resistance to nutrient dificiencies and fungus type diseases.
7. A large flower comparable to the paternal parent and larger than the maternal parent.

BRIEF DESCRIPTION OF THE DRAWING

The accompanying drawings serve, by color photographic means, to illustrate the new plant variety and wherein.

DETAILED DESCRIPTION OF THE DRAWING

Figure 1:
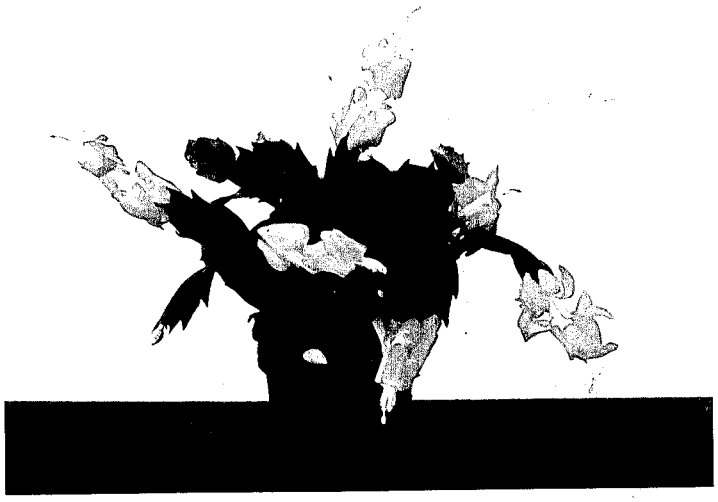
FIG. 1 is a color photograph of a potted plant of the new variety illustrating the overall appearance and form of the plant.
Figure 2:
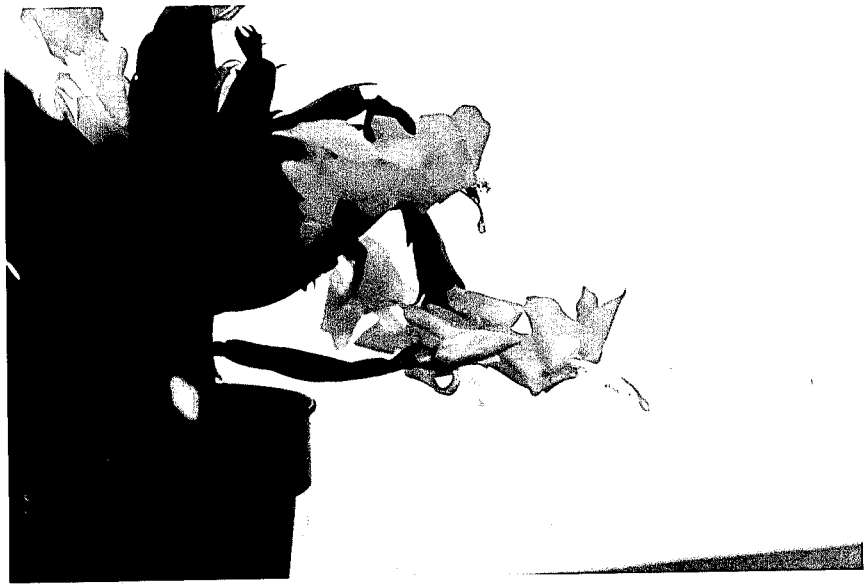
FIG. 2 is a color photograph showing a fully opened bloom of the new variety together with buds of the new variety.

The following is a detailed description of the new variety with color designations according to The Royal Horticultural Society Colour Chart issued in association with the Flower Counsel of Holland in collaboration with The Royal Horticultural Society of London. The following description is based on observations of well fertilized plants of 16–18 months of age from initial propagation which were grown under 50–70% shaded polyhouse nursery conditions at Half Moon Bay, Calif., where temperatures average from 55° to 65° F. during the summer months, and from 45° to 55° F. during the winter months.

Color designation and other values stated may deviate slightly from the stated values from flowering to flowering, but the deviations will be within the range expected from varying environmental, seasonal, and cultural conditions.

DETAILED PLANT DESCRIPTION

I. Name: *Schlumbergera truncata.*

II. Parentage:

*Maternal.—Schlumbergera truncata* "Lavender Doll" (*Zygocactus truncatus* "Lavender Doll").

*Paternal.—Schlumbergera truncata* "Maria" (*Zygocactus truncatus* "Maria").

III. Classification:

| Botanic (Britton and Rose, The Cactaceae, Constable and Co., Ltd., London, 1937, Vol. IV). (Bailey and Bailey and the staff of the Bailey Hortorium, Hortus Third, 1976) | |
|---|---|
| (1) Family: | Cactaceae |
| (2) Tribe: | Cereeae |
| (3) Sub-tribe: | Epiphyllanae |
| (4) Genus: | Schlumbergera |
| (5) Species: | Truncata (Haw.) Moran |

Commercial. - Thanksgiving cactus

IV. Form: Terrestrial, shade-loving, succulent, leafless plant with jointed and branched stems.

V. Stems:

A. *General.*—Irregular with usually mono-chotomous to di-chotomous branching of mostly upright, adventitiously rootable, irregularly revolute to flattened phylloclades that have a prominent midrib and prominently toothed lateral wings.

B. *Phylloclades.*—(1) General: Elongated with irregular involute character of the youngest phylloclades with the overall orientation that of a concave surface for one side of a phylloclade and a corresponding convex surface for the opposing side of the phylloclade, the phylloclades becoming mostly flattened with age. Phylloclades with transversely elongate, areole bearing truncated apex, with inwardly tapering basal wing margins that merge through a broad, usually pointed basal juncture with the phylloclade below and with an axillary areole associated with each tooth. (2) Midrib: General—Extends longitudinally of phylloclade and continuously through joints with laterally tapering cortex at wing insertions. Pith surrounding vascular bundles that branch and provide lateral extensions of the vascular system to marginal teeth. Texture: Smooth, waxy epidermis with wax in small embedded scales and becoming corky in basal stem areas with age. Size (18 mos)—Length: Usually between 42 and 60 mm with the average for respective plant specimens being usually between 55 and 60 mm. Thickness: usually between 2 and 4.5 mm with the average for respective plant specimens being between 3.2 and 4.2 mm. Color (at maturity): R.H.S. (144A) to (144B). (3) Wings.—general shape: Generally strongly involute when young becoming flattened with age from midrib cortex to tooth insertions with thinning taper toward margins. Margins: toothed. Texture: smooth, waxy epidermis having wax arranged in small embedded scales and becoming corky in basal stem areas with age. (4) Teeth.—General: Generally flattened and tapering along margins from wing insertions to an apex having a hyaline, pointed spine with random bending. Adaxial marginal shape: irregular varying from being distinctly concave for smaller teeth. Abaxial marginal shape: irregular, varying from being distinctly convex to generally straight or with the distal terminus being slightly convex. Orientation: usually projects distally of the phylloclade base in an alternate arrangement. Margins: entire. Texture: succulent to coriaceous with smooth, waxy epidermis having wax in small embedded scales and becoming corky in basal plant areas with age. Number: usually 6 to 8 per phylloclade. Size (18 mos).—Center thickness: usually between 0.5 and 1.5 mm. Areole to apex dimension (adaxial marginal side): usually between 2 and 8 mm. Color (at maturity): R.H.S. (144A). (5) Areoles: terminal areole-Large elongated oval-shape with several acicular bristles and a dense mat of multi-cellular hairs and several buds that may mature into either new phylloclades or flowers. The opposing ends of the areoles are located adjacent to subsidiary areoles which are in turn located at the axils of teeth that are located at the distal end of the phylloclade. Axillary areoles: acicular bristles without glochidia but having numerous short colorless or light brown, multi-cellular hairs.

VI. Buds: Unarmored, ovid and chlorophyllous when first emerging.

VII. Flowers:

A. *General.*—Sessile, zygomorphic, usually in pairs, occasionally solitary or in clusters ranging up to four, terminal, perfect, epigynous with double hypanthium and tepals having aspiral emergence as a perianth provided with a sepaloid series of free tepals, a tube laminating series of tepals, and a tube forming series of united tepals.

B. *Sepaloid series.*—(1) General: free tepals inserted on top of the ovary. (2) Shape: deltoid in outer members of the whorl and with the inner members being irregular in shape varying from elliptic to slightly oblanceolate, tips of tepals are acute in outer members of the whorl and acuminate for inner member of the whorl. Margins are entire or with sparse irregular teeth for the apical portion of the inner members of the whorl. (3) Texture: succulent and glabrous outer whorl members and grading inwardly in the whorl to thin blades with fleshy basal areas. (4) Number: usually 9 or 10. (5) Size (at full bloom): base-tip dimension-usually less than 38 mm, range for longest tepal of the sepaloid series between 32 and 38 mm. Maximum width dimension-less than 14 mm, range of maximum between 10 and 14 mm. (6) Color: outer whorl members-Varies with position of tepal within the whorl. Smallest outer whorl members with a uniform field that in color is of a magenta-rose hue. The larger outer whorl members are characterized by violet-red basal areas merging distally with red hued marginal and apical zones. The outer whorl members are basally R.H.S. (50A) magenta to (57B), with the marginal and distal zones being R.H.S. (57A) with the transition zone of color fusion between the basal and marginal areas being R.H.S. (50B) to (57B). Inner whorl members have basal areas dominated by R.H.S. (50A) intensifying to R.H.S. (57B) immediately distal to the basal area. Marginal areas are dominated by R.H.S. (57A) intergrading to R.H.S. (57B). (7) Orientation at full bloom: generally acute to slightly reflexed.

C. *Tube laminating series.*—(1) General: tepals inserted on ovary and basally united below the throat as outer laminations on the perianth tube and with progressively greater amounts of basal fusion inwardly in the whorl. (2) Shape: grading inwardly in whorl with progressively longer base-tip dimensions and with linear to oblanceolate tepals and with the free portion of the blade being linear to slightly anceolate, tip narrow to broadly acute generally with a short apiculate ultimate apex. Margins mostly entire at base with very small, sparse and irregular teeth on the margin from near the middle of the tepal to the apex, (3) Texture: succulent and fleshy basal area, thin and soft blades. (4) Number: usually 4 to 6. Size (at full bloom): Base—tip usually between 30 and 59 mm. Maximum width dimensions: usually between 14 and 18 mm. (5) Color: tepals with basal areas R.H.S. (50A) distally becoming more intensely colored R.H.S. (58B). The marginal area of the blades of the tube laminating series is R.H.S. (57A), integrading to R.H.S. (57B) as the marginal and distal basal areas merge.

D. *Tube forming series.*—(1) General: tepals basally united to form perianth tube that is inserted on ovary and equipped with a vestigial carina at the throat. (2) Shape: perianth tube-Elongated and ellipsoidal in cross-section. Blades linear to slightly oblanceolate, tips acute to slightly acuminate. Margins basally entire, apically with small irregular teeth. Carina: vestigial at throat of perianth tube. (3) Texture: perianth tube-thick, succulent, slightly ribbed at point of lateral fusion of tepals. Blades: proximally fleshy, distally thin and soft. Carina: fleshy. (4) Blade number: usually 10. (5) Size (at full bloom): perianth tube—base to keel length. Usually between 34 and 40 mm along axis of tube with average length difference between measurements along dorsal and ventral sides for respective specimens usually between 2.5 and 5 mm. Internal major axis (at throat): usually between 8 and 11 mm when measured perpendicular to axis of perianth tube. Internal minor axis (at throat): usually between 4 and 8 mm when measured perpendicular to axis of perianth tube. Blades—length (keel to tip): usually between 33 and 40 mm. Width (maximum): usually between 12 and 15 mm. (6) Color (at full bloom): perianth tube-usually translucent white with lines marking laterial fusion of tepals R.H.S. (66C). Blades—Tepal blades with marginal blade areas which in color are dominated by magenta to violet rose that merges with carmine red for the basal blade area that extends distally of the throat. The basal area R.H.S. (51A) distally becomes R.H.S. (57B) and merges with the marginal area R.H.S. (57A). Carina: characterized by R.H.S. (66C) to (57C). Orientation at full bloom: reflexed.

E. *Androecium (stamens).*—(1) General: numerous excerted and diadelphous stamens with one group having filaments usually basally fused to the perianth tube and the other group having filaments basally united to form a nectary housing, thin annulus around the style and which is provided with a thin, slightly deflexed, irregularly toothed margin at the throat of the annulus. (2) Stamen number: tube attached group-usually between 97 and 105. Basally united group-usually between 19 and 26. (3) Filament general: translucent white and glabrous with anther connective. Shape: long, slender, gradually tapering from base to anther connective. Texture: glabrous and smooth. Color: translucent white. Size (at full bloom) length: tube attached group-usually between 40 and 55 mm. Basally united group: usually between 45 and 52 mm. Diameter: usually between 0.2 and 0.3 mm intermediate the opposing ends. (4) Anthers generally: adnate with four longitudinally dehiscent pollen sacs. Shape: elongated. Texture: waxy. Color (post dehiscence, pollen color): usually R.H.S. (11C) to (11D).

F. *Gynoecium (pistil).*—(1) General: compound, parietal placentation with a united style surrounded by an annular diffuse nectary at its insertion. (2) Style general: stout and inserted in ovary. Shape: elongated cylindrical and generally tapering. Texture: fleshy and glabrous. Color: proximal end is R.H.S. (57A) gradually changing to R.H.S. (57C) at the distal end of the style. Size (at full bloom): Length: usually about 56 mm. Diameter: usually between 0.6 and 0.8 mm intermediate the opposing ends. (3) Stigma—General: exserted and erect with usually 6 or 7 inner marginally adhering lobes. Shape: elongated and tapering toward lobe tips and having relatively blunt apices. Texture: fleshy with short glutinous hairs. Color: area proximal to point of attachment of stigma to style R.H.S. (61B) distally decreasing in intensity to R.H.S. (61C) at the tips of the stigma lobes. Size (lobe length at full bloom): usually between 2.8 and 4.2 mm. (4) Ovary General: epigynous with thin epidermis and distally located concavity and with single cavity usually having 6 or 7 carpels with numerous ovules. Shape: terete to ovoid, broadening from insertion to floral end. Texture: succulent and glabrous with thin epidermis. Color: mostly translucent white or very light green-yellow R.H.S. (150B) with portion immediately distal to point of attachment to phylloclade R.H.S. (65A) and portion immediately bordering attachment of tepals R.H.S. (50A). Size (at full bloom)—Length (insertion to concavity base): usually between 9 and 11 mm. Major axis (distal end of concavity): usually between 7 and 10 mm. Minor axis (distal end of concavity): usually between 6 and 9 mm.

The following is a general description of a flower of the new plant variety grown at Half Moon Bay, Calif., under greenhouse nursery conditions.

Bloom life: 8 Days.

Sepaloid series of tepals:

(1) *Number.*—10.

(2) *Size (at full bloom).*—Maximum base-tip dimension: 37 mm. Minimum base—tip dimension: 11 mm.

(3) *Color.*—Most outer whorl basally R.H.S. (50A) to R.H.S. (57B), marginal and distal areas R.H.S. (57A) with transition zone of R.H.S. (50B) to R.H.S. (57B) between basal and marginal areas. (54A) becoming more intensely colored R.H.S. Inner whorl members basally R.H.S. (57B) distally, marginal zones R.H.S. (57A) with transition zone of R.H.S. (57B).

Tube laminating series:

(1) *Number.*—6.

(2) *Size (at full bloom).*—Maximum base-tip dimension: 57 mm. Minimum base-tip dimension: 34 mm. Maximum width dimension: 17 mm. Minimum width dimension: 12 mm.

(3) *Color.*—Basally R.H.S. (50A) (58A), marginal blade area R.H.S. (57A) (57B) (66A).

Tube forming series:

(1) *Number.*—10.

(2) *Size (at full bloom) Perianth tube.*—Base to throat length 36 mm. Interior major axis (at throat): 10 mm. Interior minor axis (at throat): 7 mm. Blades: maximum length (throat to tip) 38 mm. Minimum length (throat to tip): 30 mm. Maximum width: 15 mm. Minimum width: 13 mm.

(3) *Color.*—Perianth tube: translucent white with the lines of lateral fusion of tepals R.H.S. (66C). Blades: basally R.H.S. (51A) distally becoming R.H.S. (57B), marginal areas are R.H.S. (57A). Carina: R.H.S. (56C) to (57C).

Androecium:

(1) *Stamen number.*—Tube attached group: 99. Basally united group: 22.

(2) *Filaments.*—Color: translucent white. Size (at full bloom): Length-tube attached group: 49 mm (avg.). Basally united group: 46 mm (avg.). Diameter: 0.25 mm (avg.).

(3) *Anthers.*—Color (post dehiscense): R.H.S. (11C) to (11D).

Gynoecium:

(1) *Style.*—Color: Proximal end R.H.S. (57A), distally becoming R.H.S. (57C). Size (at full bloom): Length—63 mm. Diameter—0.8 mm intermediate the two opposing ends.

(2) *Stigma.*—Color: Proximally R.H.S. (61B) decreasing in intensity distally to R.H.S. (61C). Size (lobe length.) 4.0 mm (avg.).

(3) *Ovary.*—Color: Translucent white to very light green-yellow R.H.S. (150B) with zone immediately distal to attachment with phylloclade R.H.S. (65A) and the portion immediately bordering attachment of tepals R.H.S. (50A). Length (insertion to concavity base)—10 mm. Major axis (distal end of concavity)—9 mm. Minor axis (distal end of concavity)—8 mm.

The following is a general description of a specimen of the new plant variety that was grown from the propagation of a single phylloclade in a nursery at Half Moon Bay, Calif.

Age from initial propagation: 18 months.
Branches from propagated cutting: 5.
Total number of phylloclades grown from cutting: 53.

General:

| Branch No. | No. of Phylloclades | Max. Length | No. of Tips |
|---|---|---|---|
| 1 | 19 | 215 mm | 8 |
| 2 | 15 | 190 mm | 7 |
| 3 | 9 | 200 mm | 3 |
| 4 | 7 | 175 mm | 3 |
| 5 | 3 | 132 mm | 1 |

Midribs:

| Branch No. | Length (avg.) | Thickness (avg.) |
|---|---|---|
| 1 | 50.0 mm | 3.9 mm |
| 2 | 45.0 mm | 3.1 mm |
| 3 | 46.6 mm | 3.2 mm |
| 4 | 42.0 mm | 2.9 mm |
| 5 | 41.6 mm | 2.2 mm |

Wings:

| Branch No. | Center Thickness (avg.) | Max. Width (avg.) |
|---|---|---|
| 1 | 1.3 mm | 34.0 mm |
| 2 | 1.28 mm | 30.1 mm |
| 3 | 1.0 mm | 25.2 mm |
| 4 | 1.1 mm | 33.0 mm |
| 5 | 0.9 mm | 29.2 mm |

Teeth:

| Branch No. | No./Phylloclade (avg.) | Center Thickness (avg.) | Areole to Apex Dimension (avg.) |
|---|---|---|---|
| 1 | 6.0 | 0.75 mm | 3.0 mm |
| 2 | 5.5 | 0.6 mm | 3.7 mm |
| 3 | 5.0 | 0.6 mm | 3.7 mm |
| 4 | 4.6 | 0.5 mm | 2.3 mm |
| 5 | 5.0 | 0.65 mm | 1.0 mm |

Phylloclade color: R.H.S. (146A).

I claim:

1. The new and distinct hybrid plant variety of the Cactaceae family substantially as herein shown and described.

* * * * *

UNITED STATES PATENT AND TRADEMARK OFFICE

CERTIFICATE OF CORRECTION

PATENT NO. : PP 7,367

DATED : October 23, 1990

INVENTOR(S) : Harry Higaki

It is certified that error appears in the above-identified patent and that said Letters Patent is hereby corrected as shown below:

Column 6, line 19, after the word "filaments" delete ---usually---

Column 7, line 22, change "(54A)" to ---(50A)---

Column 7, line 22, before "(54A)" insert ---Inner whorl members basally R.H.S.---

Column 7, line 23, before "(57B)" delete ---Inner whorl members basally R.H.S.---

Signed and Sealed this

Third Day of March, 1992

*Attest:*

HARRY F. MANBECK, JR.

*Attesting Officer*

*Commissioner of Patents and Trademarks*